United States Patent [19] [11] 4,353,916
Uematsu et al. [45] Oct. 12, 1982

[54] BENZOTHIAZOL-2-ONES AND PHYTOPATHOGENIC FUNGICIDAL USE THEREOF

[75] Inventors: Tamon Uematsu, Toyonaka; Satoru Inoue, Nishinomiya; Norihisa Yamashita, Takarazuka, all of Japan

[73] Assignee: Sumitomo Chemical Company, Ltd., Japan

[21] Appl. No.: 199,222

[22] Filed: Oct. 21, 1980

Related U.S. Application Data

[63] Continuation of Ser. No. 866,401, Dec. 30, 1977, abandoned.

[30] Foreign Application Priority Data

Jan. 17, 1977 [JP] Japan .................................. 52-4296
Apr. 5, 1977 [JP] Japan .................................. 52-39308
Sep. 2, 1977 [JP] Japan .................................. 52-106192

[51] Int. Cl.³ .................. A01N 43/78; C07D 277/68
[52] U.S. Cl. ..................................... 424/270; 548/165
[58] Field of Search ....................... 548/165; 424/270

[56] References Cited

U.S. PATENT DOCUMENTS 1,962,109  6/1934  Alvord ................................ 424/270
2,922,794  1/1960  Model et al. ........................ 548/173
3,629,428  12/1971 Seki et al. ........................... 424/270
3,740,191  6/1973  Wave .................................. 424/270

FOREIGN PATENT DOCUMENTS 847360   10/1939  France ............................... 424/270
14-22730 10/1939  Japan ................................. 424/270
830902   3/1960   United Kingdom ................ 424/270
855389   11/1960  United Kingdom ................ 424/270
956571   4/1964   United Kingdom ................ 424/270
1020307  2/1966   United Kingdom ................ 424/270

Primary Examiner—D. B. Springer
Attorney, Agent, or Firm—Wenderoth, Lind & Ponack

[57] ABSTRACT 3,4-Disubstituted benzoxa(thia)zole-2-one derivatives of the formula:

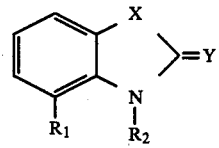

wherein $R_1$ is a halogen atom or methyl group, $R_2$ is a methyl or ethyl group and X and Y are individually an oxygen or sulfur atom, and their preparation and use as a fungicide.

7 Claims, No Drawings

BENZOTHIAZOL-2-ONES AND PHYTOPATHOGENIC FUNGICIDAL USE THEREOF

This is a continuation of Ser. No. 866,401 filed Dec. 30, 1977, now abandoned.

The present invention relates to 3,4-disubstituted benzothiazole-2-one or benzoxazole-2-one derivatives (hereinafter referred to as "benzoxa(thia)zolone derivative(s)") of the formula;

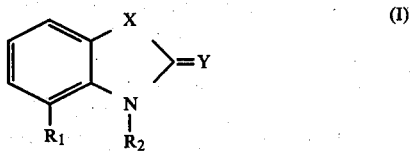

wherein $R_1$ is a halogen atom (e.g. fluorine, chlorine, bromine) or methyl group, $R_2$ is a methyl or ethyl group and X and Y are individually an oxygen or sulfur atom, and their preparation and use as a fungicide.

It is already known that some of benzothiaziolone or benzoxazolone derivatives have a biological activity on certain harmful life (cf. Pharmazie, 1963, 281-283, Japanese Patent Publication No. 11518/1965 and Yakugaku Zasshi, vol. 79, 931-933). As the result of extensive study, it has now been found that the benzoxa(thia)zolone derivatives (I) having substituents at both 3-and 4-positions do exhibit an antimicrobial activity which is widely applicable and markedly superior as compared with the homologues against phyto-pathogenic microorganisms which do great damage to cultivation of agricultural crops, for example on Phycomycetes (e.g. *Mucor spinescens*), Ascomycetes (e.g. *Neurospora crassa, Giberella zeae, Sclerotinia sclerotiorum, Mycosphaerella melonis, Glomerella cingulata, Giberella fujikuroi, Cochliobolus miyabeanus, Venturia inaqualis*), Basidiomycetes (e.g. *Corticium rolfsii*), Funji imperfecti (e.g. *Aspergillus niger, Fusarium oxysporum* f. cucumerinum, *Cladosporium cucumerinum, Pyricularia oryzae, Collectotrichum lagenarium, Helminthosporium sigmoideum*) and other bacteria (e.g. *Xanthomonas oryzae*).

The benzoxa(thia)zolone derivatives (I) are especially effective in controlling rice blast (*Pyricularia oryzae*) and stem rot of rice (*Helminthosporium sigmoideum*) which are serious diseases of rice, they have a property to be applicable by any of the three application techniques of foliar application, submerged application and soil application, and further that they have a high controlling effect. They have good vapor action, it is also possible to adopt an application making the most of this particular property thereinto. Furthermore, the benzoxa(thia)zolone derivatives (I) possess a very strong effect with such rapidity and long persistency that can not be obtained from the well-known foliar-applied, water-surface-applied and soil applied fungicides for rice blast, and in addition show extremely low toxicity to warm-blooded animals (e.g. mice, rats, chickens) and a fish (e.g. carps, killifishes) and hardly remain in the body of crops.

A main object of the present invention is to provide novel benzoxa(thia)zolone derivatives (I), which are useful as fungicides. Another object of this invention is to provide a process for preparing such benzoxa(thia)zolone derivatives(I). A further object of the invention is to provide fungicidal compositions containing such benzoxa(thia)zolone derivatives (I). These and other objects and advantages of the invention will become apparent from the foregoing and subsequent descriptions.

The benzoxa(thia) zolone derivatives (I) of the present invention may be prepared by various methods, of which typical examples will be described below.

PROCEDURE A

The 3,4-disubstituted benzoxa(thia)zolone of the formula;

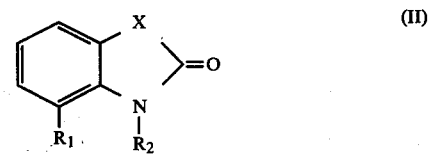

wherein $R_1$, $R_2$ and X are each as defined above, can be prepared by alkylating a corresponding 3-unsubstituted benzoxa(thia)zolone of the formula;

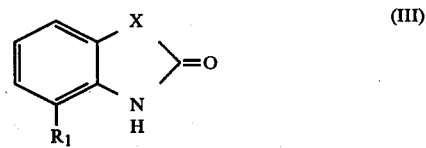

wherein $R_1$ and X are each as defined above, with an alkylating agent (e.g. dimethyl sulfate, diethyl sulfate, methyl bromide, ethyl bromide, methyl iodide, ethyl iodide) at a temperature from 0° C. to 150° C. in the presence of a base (e.g. potassium tert-butoxide, sodium methoxide, sodium ethoxide, sodium hydride) in an inert solvent (e.g. benzene, toluene, xylene, tetrahydrofuran, dioxane, ether or a mixture thereof), in the presence of a base (e.g. sodium methoxide, sodium ethoxide, sodium hydroxide, potassium hydroxide) in a solvent (e.g. methanol, ethanol or a mixture thereof) or in the presence of a base (e.g. sodium hydroxide, potassium hydroxide) in a solvent (e.g. water, water soluble organic solvent such as methanol, ethanol, dioxane or a mixture thereof) for 0.5 to 10 hours.

PROCEDURE B

The 3,4-disubstituted benzoxa(thia)zolone (II) can be prepared by alkylating a 2-alkylthiobenzoxa(thia)zole of the formula;

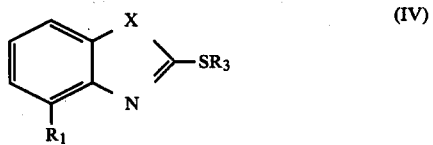

wherein $R_3$ is a lower alkyl group (e.g. methyl, ethyl, propyl, butyl) and $R_1$ and X are each as defined above, with an alkylating agent (e.g. methyl bromide, ethyl bromide, methyl iodide, ethyl iodide, dimethyl sulfate, diethyl sulfate, methyl p-toluenesulfonate, ethyl p-toluenesulfonate) at a temperature from 0° C. to 100° C. in the presence or absence of an inert solvent (e.g. benzene, toluene, xylene, ethanol, methanol, water, dioxane, tetrahydrofuran, ether or a mixture thereof) for 0.5 to 15 hours to obtain a corresponding quaternary salt, and then decomposing the salt in an aqueous sodium hydroxide or potassium hydroxide solution.

PROCEDURE C

The 3,4-disubstituted benzothiazolone of the formula;

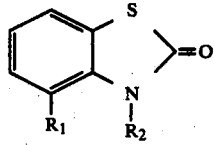

wherein $R_1$ and $R_2$ are each as defined above, can be prepared by heat-decomposition of a 2-nitrosoiminobenzothiazole of the formula;

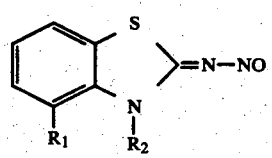

wherein $R_1$ and $R_2$ are each as defined above, at a temperature from 50° C. to 200° C. in the presence or absence of an inert solvent (e.g. toluene, xylene) thereby gradually generate nitrogen gas.

PROCEDURE D

The 3,4-disubstituted benzoxa(thia)zolone (II) can be prepared by reacting an aniline derivative of the formula;

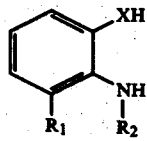

wherein $R_1$, $R_2$ and X are each as defined above, with phosgene at a temperature from 0° C. to 100° C. in an inert solvent (e.g. water, dioxane, benzene, toluene, xylene or a mixture thereof) in the presence of a base (e.g. sodium hydroxide, potassium hydroxide, pyridine, methylamine, ethylamine, ammonia, piperidine, aniline itself as a starting material) for 10 minutes to 3 hours, followed by filtration of the hydrochloric acid salt of the base and removal of the solvent by evaporation.

PROCEDURE E

The 3,4-disubstituted benzoxazolone of the formula;

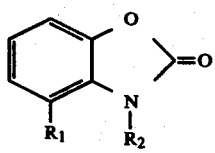

wherein $R_1$ and $R_2$ are each as defined above, can be prepared by reacting an aminophenol derivative of the formula;

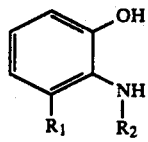

wherein $R_1$ and $R_2$ are each as defined above, with a mineral acid (e.g. hydrochloric acid) at a room temperature (0° C. -25° C.) in a solvent (e.g. diethyl ether, methanol, ethanol, benzene) to obtain a corresponding acid salt, and then heating the salt with urea at the temperature from 100° C. to 200° C. in an inert solvent (e.g. 1,3-butanediol) for 1 to 5 hours, acidifying the reaction mixture with a mineral acid, extracting the acidic mixture with a suitable organic solvent (e.g. diethyl ether, chloroform, benzene, toluene, xylene), drying the extract, and removing the solvent by evaporation.

PROCEDURE F

The 3,4-disubstituted benzoxa(thia)zolethione of the formula;

(X)

wherein $R_1$, $R_2$ and X are each as defined above, can be prepared by heating the 3,4-disubstituted benzoxa(thia)zolone (II) with phsphorus pentasulfide at a temperature from 60° to 150° C. in an inert solvent (e.g. pyridine, benzene, toluene, xylene, chloroform, carbon tetrachloride, mixture thereof) for a suitable period of time (e.g. 1 to 10 hours), followed by filtration and removal of the solvent by evaporation.

PROCEDURE G

The 3,4-disubstituted benzoxa(thia)zolethione (X) can be prepared by heating a 2-alkylthio-benzoxa(thia)zole of the formula;

(XI)

wherein $R_1$, $R_2$ and X are each as defined above, at a temperature from 100° C. to 250° C. in the presence or absence of an inert solvent (e.g. nitrobenzene, dichlorobenzene) and, if necessary, in the presence of a catalyst (e.g. methyliodide, methylbromide, iodine, bromine) for a suitable period of time (e.g. 1 to 10 hours).

PROCEDURE H

The 3,4-disubstituted benzoxa(thia)zolethione (X) can be prepared by alkylating the 2-alkylthio-benzoxa(thia)zole (IV) with an alkylating agent (e.g. dimethyl sulfate, diethyl sulfate, methyl p-toluenesulfonate, ethyl p-toluenesulfonate, methyl iodide, ethyl iodide, methyl bromide, ethyl bromide) at a temperature from 0° C. to 100° C. in the presence or absence of an inert solvent (e.g. benzene, toluene, xylene, ethanol, methanol, water, dioxane, tetrahydrofuran, diethyl ether or a mixture thereof) for 0.5 to 10 hours to obtain a corresponding quaternary salt, and then decomposing the salt in an aqueous sodium hydrogen sulfide or sodium sulfide solution.

PROCEDURE I

The 3,4-disubstituted benzoxa(thia)zolethione (X) can be prepared by mixing the aniline derivative (VII) with an equivalent or excessive molar amount of the thiophosgene at a temperature from 0° to 50° C., in the presence of a base (e.g. sodium hydroxide, potassium hydroxide) in an inert solvent (e.g. water, benzene, toluene, xylene or a mixture thereof), stirring the mixture for 0.5 to 3 hours, adding water to the mixture, extracting the resulting mixture with an organic solvent (e.g. benzene, chloroform, diethyl ether, toluene) and then washing the extract with water, followed by drying and solvent removal by evaporation.

PROCEDURE J

The 3,4-disubstituted benzoxa(thia)zolone (II) can be prepared by heating a 2-alkoxybenzoxa(thia)zole of the formula;

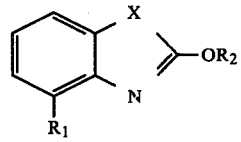
(XII)

wherein $R_1$, $R_2$ and X are each as defined above, at a temperature from 100° C. to 250° C. in the presence or absence of an inert solvent (e.g. nitrobenzene, dichlorobenzene) for 1 to 10 hours.

The benzoxa(thia)zolone derivatives (I) thus produced may be purified, if necessary, by a per se conventional procedure such as recrystallization, distillation and column chromatography.

The starting materials are obtainable, for instance, by the process as described in J.O.C. 18 1092–1102, Bull. Soc. Chim. Fr., 3044–3051 (1973), or Ber. 64 1664 (1931).

Specific examples of the benzoxa(thia)zolone derivatives (I) thus prepared are shown in Table 1.

TABLE 1

| Procedure | Compound No. | Chemical structure | (Molecular equation) | m.p. (°C.) | Calcd. (%) C | H | N | Halogen | Found (%) C | H | N | Halogen |
|---|---|---|---|---|---|---|---|---|---|---|---|---|
| B | 1 | [structure with S, =O, CH3, CH3] | ($C_9H_9NSO$) | 124 | 60.30 | 5.07 | 7.82 | | 60.17 | 5.20 | 7.79 | |
| A | 2 | [structure with S, =O, Cl, CH3] | ($C_8H_6NSOCl$) | 131–132 | 48.12 | 3.03 | 7.02 | 17.76 | 48.21 | 3.04 | 7.11 | 17.58 |
| C | 3 | [structure with S, =O, Cl, C2H5] | ($C_9H_8NSOCl$) | 98–99 | 50.58 | 3.78 | 6.56 | 16.59 | 50.62 | 3.79 | 6.33 | 16.45 |
| F | 4 | [structure with S, =S, CH3, CH3] | ($C_9H_9NS_2$) | 159–161 | 55.34 | 4.65 | 7.17 | | 55.11 | 4.70 | 7.21 | |
| G | 5 | [structure with S, =S, Cl, CH3] | ($C_8H_6NS_2Cl$) | 164–166 | 44.54 | 2.81 | 6.49 | 16.43 | 44.67 | 2.80 | 6.51 | 16.29 |
| H | 6 | [structure with S, =S, Cl, C2H5] | ($C_9H_8NS_2Cl$) | 76–77 | 47.05 | 3.52 | 6.09 | 15.43 | 47.20 | 3.52 | 6.05 | 15.29 |
| D | 7 | [structure with O, =O, CH3, CH3] | ($C_9H_9NO_2$) | 99 | 66.24 | 5.57 | 8.58 | | 66.13 | 5.60 | 8.47 | |

TABLE 1-continued

| Procedure | Compound No. | Chemical structure | (Molecular equation) | m.p. (°C.) | Calcd. (%) C | H | N | Halogen | Found (%) C | H | N | Halogen |
|---|---|---|---|---|---|---|---|---|---|---|---|---|
| A | 8 | 4-Cl, N-CH₃ benzoxazolone | (C₈H₆NO₂Cl) | 95 | 52.33 | 3.30 | 7.63 | 19.31 | 52.24 | 3.15 | 7.57 | 19.11 |
| E | 9 | 4-Cl, N-C₂H₅ benzoxazolone | (C₉H₈NO₂Cl) | 57 | 54.70 | 4.09 | 7.08 | 17.94 | 54.82 | 4.11 | 7.20 | 17.99 |
| I | 10 | 4-CH₃, N-CH₃ benzoxazole-2-thione | (C₉H₉NOS) | 137–139 | 60.30 | 5.07 | 7.81 | | 60.41 | 5.20 | 7.83 | |
| G | 11 | 4-Cl, N-CH₃ benzoxazole-2-thione | (C₈H₆NOSCl) | 98–99 | 48.12 | 3.04 | 7.01 | 17.76 | 48.01 | 3.11 | 7.22 | 17.59 |
| H | 12 | 4-Cl, N-C₂H₅ benzoxazole-2-thione | (C₉H₈NOSCl) | 83–84 | 50.58 | 3.78 | 6.55 | 16.59 | 50.60 | 3.81 | 6.44 | 16.64 |
| A | 13 | 4-F, N-CH₃ benzothiazolone | (C₈H₆NOSF) | 68–69 | 52.44 | 3.31 | 7.64 | | 52.51 | 3.23 | 7.58 | |
| A | 14 | 4-Br, N-CH₃ benzothiazolone | (C₈H₆NOSBr) | 139–140 | 39.36 | 2.48 | 5.74 | 32.73 | 39.15 | 2.53 | 5.94 | 32.57 |
| F | 15 | 4-Br, N-CH₃ benzothiazole-2-thione | (C₈H₆NOS₂Br) | 169 | 36.93 | 2.33 | 5.38 | 30.71 | 36.79 | 2.45 | 5.22 | 30.90 |
| F | 16 | 4-F, N-CH₃ benzothiazole-2-thione | (C₈H₆NOS₂F) | 124 | 48.22 | 3.04 | 7.03 | 9.53 | 48.15 | 3.11 | 7.20 | 9.68 |

Practical and presently preferred embodiments of the preparation of the benzoxa(thia)zolone derivatives (I) and illustratively shown in the following examples.

EXAMPLE 1 (PROCEDURE A)

To a mixture of 2.4 g. (0.1 mole) of sodium hydride in 50 ml. of dry xylene was gradually added. 14.9 g. (0.1 mole) of 4-chlorobenzothiazolone under reflux and stirring, followed by boiling for 1 hour with stirring. Thereafter, a solution of 12.6 g. (0.1 mole) of dimethyl sulfate in 10 ml. of dry xylene was added thereto from a dropping funnel. The reaction mixture was boiled for further 2 hours with stirring, cooled to room temperature, poured into 300 ml. of water, and the mixture was vigorously shaken in a separating funnel. The separated xylene layer was washed with water, separated from the aqueous layer, dried over magnesium sulfate and filtered, followed by removal of the solvent by evaporation. The crystal obtained was recrystallized from n-hexane to obtain 15.5 g. of colorless 3-methyl-4-chlorobenzothiazolone as crystals (m.p. 131°–132° C.).

EXAMPLE 2 (PROCEDURE B)

18.0 g. (0.092 mole) of 2-methylthio-4-methylbenzothiazole and 15.1 g. (0.12 mole) of dimethyl sulfate were mixed without a solvent, stirred at 80° C. for 10 hours and then ice-cooled. The crystallized quaternary salt was dissolved in 10 ml. of water and the solution was made alkaline (pH 10) with a conc. aqueous sodium hydroxide solution. The precipitated crystals were filtered, washed with water, dried and recrystallized from n-hexane to obtain 15.8 g. of colorless 3,4-dimethylbenzothiazolone as crystals (m.p. 124° C.).

EXAMPLE 3 (PROCEDURE C)

2.0 g. of 2-nitrosoimino-3-ethyl-4-chlorobenzothiazole was placed in a 200-ml. flask and gradually heated to 180° C. in an oil bath to generate nitrogen gas. When the generation of nitrogen gas stopped in about 1 hour, the reaction mass was cooled to room temperature and the residue obtained was recrystallized from n-hexane to obtain 1.4 g. of colorless 3-ethyl-4-chlorobenzothiazolone as crystals (m.p. 98°–99° C.).

EXAMPLE 4 (PROCEDURE D)

1.37 g. (0.01 mole) of 2-methylamino-m-cresol was dissolved in 20 ml. of 1 N aqueous sodium hydroxide solution, followed by cooling with ice. Thereafter, a solution of 1 g. (0.01 mole) of phosgene in 5 ml. of dioxane was added dropwise thereto at 0° to 5° C. with vigorous stirring. After vigorous stirring at room temperature for 30 minutes, the precipitated crystals were filtered, washed with water, dried and recrystallized from n-hexane to obtain 1.5 g. of colorless 3,4-dimethylbenzoxazolone (m.p. 99° C.).

EXAMPLE 5 (PROCEDURE E)

1.5 g. (0.01 mole) of 2-ethylamino-m-cresol was dissolved in 30 ml. of ethyl ether, and an excess of hydrogen chloride was blowed into the resulting solution at 20° C. The precipitated 2-ethylamino-m-cresol hydrochloride was filtered, washed with ethyl ether and dried. 1.8 g. of this crystal and 600 mg. (0.01 mole) of urea were charged in 10 ml. of 1,3-butanediol, and the mixture was heated at 170° C. for 2.5 hours with stirring. The reaction mixture was then cooled to room temperature and acidified to pH of 1 with 10% aqueous hydrochloric acid. The solution was extracted with three 30 ml. portions of ethyl ether, and the extract was washed with water, dried over magnesium sulfate and freed from the solvent by evaporation. The residue obtained was recrystallized from n-hexane to obtain 1.1 g. of colorless 3-ethyl-4-chlorobenzoxazolone (m.p. 57° C.).

EXAMPLE 6 (PROCEDURE F)

1.0 g. of 3,4-dimethylbenzothiazolone and 2.5 g. of phosphorus pentasulfide were thoroughly mixed and stirred in 5 ml. of a dry xylene at 140° C. for 4 hours. The reaction mixture was then filtered hot through celite and washed with a hot xylene. The solvent was removed from the filtrate under reduced pressure and the crystals obtained were recrystallized from ethanol to obtain 0.82 g. of the objective 3,4-dimethylbenzothiazolethione (m.p. 159°–161° C.).

EXAMPLE 7 (PROCEDURE G)

A mixture of 1.0 g. of 2-methylthio-4-chlorobenzothiazole and 0.1 g. of iodine was heated at 220° C. for 5 hours on an oil bath and then cooled to room temperature. The crystals obtained were recrystallized from ethanol to obtain 0.89 g. of the objective 3-methyl-4-chlorobenzothiazolethione (m.p. 164°–166° C.).

EXAMPLE 8 (PROCEDURE H)

A mixture of 1.0 g. of 2-ethylthio-4-chlorobenzothiazole and 1.0 g. of diethyl sulfate was stirred at 80° C. for 4 hours, cooled to room temperature and then dissolved in 10 ml. of water. To the resulting aqueous solution was dropwise added an aqueous solution of 0.41 g. of NaSH in 1 ml. of water at 0° C. to 7° C. The mixture was stirred at room temperature for 5 hours. The precipitated crystals were filtered, washed with water, dried and recrystallized from ethanol to obtain 0.88 g. of the objective 3-ethyl-4-chlorobenzothiazolethione (m.p. 76°–77° C.).

EXAMPLE 9 (PROCEDURE G)

A mixture of 1.0 g. of 2-methylthio-4-chlorobenzoxazole and 0.1 g. of methyl iodide was heated at 200° C. for 7 hours on an oil bath and then cooled to room temperature. The crystals obtained were recrystallized from methanol to obtain 0.87 g. of the objective 3-methyl-4-chlorobenzoxazolethione (m.p. 98°–99° C.).

EXAMPLE 10 (PROCEDURE H)

A mixture of 1.0 g. of 2-ethylthio-4-chlorobenzoxazole and 1.1 g. of diethyl sulfate was stirred at 100° C. for 3 hours, cooled to room temperature and then dissolved in 10 ml. of water. To the resulting aqueous solution was dropwise added an aqueous solution of 0.63 g. of $Na_2S$ in 1 ml. of water at 0° C. to 7° C. The mixture was stirred at room temperature for 5 hours. The precipitated crystals were filtered, washed with water, dried and recrystallized from methanol to obtain 0.84 g. of the objective 3-ethyl-4-chlorobenzoxazolethione (m.p. 83°–84° C.).

EXAMPLE 11 (PROCEDURE I)

1.37 g. of 2-methylamino-3-methylphenol was dissolved in an aqueous solution of 0.4 g. of sodium hydroxide in 30 ml. of water. Thereafter, a solution of 1.2 g. of thiophosgene in 30 ml. of toluene was added dropwise to the above aqueous solution at 10° C. After stirring at room temperature for 1 hour, the reaction solution was separated into two layers. The toluene layer was washed with water and dried, and the toluene was removed under reduced pressure. The crystals obtained were recrystallized from ethanol to obtain 1.4 g. of the objective 3,4-dimethylbenzoxazolethione (m.p. 137°–139° C.).

EXAMPLE 12 (PROCEDURE J)

1.5 g. of 2-methoxy-4-bromobenzothiazole was heated at 160° C. for 5 hours on an oil bath and then cooled to room temperature. The crystals obtained were recrystallized from hexane to obtain 1.3 g. of the objective 3-methyl-4-bromobenzothiazolone (m.p. 139°–140° C.).

In the actual application as a fungicide, the benzoxa(thia)zolone derivatives (I) may be used alone without incorporation of any other ingredient such as a carrier or a diluent, but for easier application, are used in any of ordinarily adopted forms such as, for example, dusts, wettable powders, oil sprays, aerosols, tablets, emulsifiable concentrates, granules and fine granules. In order to formulate these preparations, the benzoxa(thia)zolone derivatives (I) may be admixed with such solid carriers or diluents as mineral powders (e.g. talc, bentonite, montmorillonite, clay, kaolin, diatomaceous earth, mica, apatite, vermiculite, gypsum, calcium carbonate, pyrophyllite, sericite, pumice, sulfur, active carbon, slaked lime), plant powders (e.g. soybean, wheat, wood, walnut shell, saw dust, bran, bark, plant extract residue, tobacco, starch, crystalline cellulose), polymeric material powders (e.g. petroleum resin, polyvinyl chloride, dammar gum, ketonic resin), fiber products (e.g. paper, corrugated cardboard, old rags), chemical fertilizers (e.g. ammonium sulfate, ammonium phosphate, ammonium nitrate, urea, ammonium chloride), alumina or wax, or with such liquid carriers or diluents as alcohols (e.g. methanol, ethanol. ethylene glycol, benzyl alcohol), aromatic hydrocarbons (e.g. benzene, toluene, xylene, methylnaphthalene), aliphatic hydrocarbons (e.g. kerosene, hexane), chlorinated hydrocarbons (e.g. chloroform, carbon tetrachloride, monochlorobenzene), ethers (e.g. diethyl ether, dioxane, tetrahydrofuran, ethylene glycol ethyl ether), ketones (e.g. acetone, methyl ethyl ketone, cyclohexanone), esters (e.g. ethyl acetate, butyl acetate, ethylene glycol acetate), acid amides (e.g. N,N-dimethylformamide), nitriles (e.g. acetonitrile) or sulfoxides (e.g. dimethylsulfoxide). If necessary, other additives such as binding and/or dispersing agent (e.g. gelatin, casein, sodium alginate, CMC, starch, gum arabic powder, lignosulfonate, bentonite, polyoxypropyleneglycol ether, polyvinyl alcohol, pine oil, liquid or solid paraffine), stabilizer (e.g. isopropyl phosphate, tricresyl phosphate, tall oil, epoxidized oil, surfactant, fatty acid, fatty acid ester) or emulsifier (e.g. alkyl sulfonate, polyoxyethylene alkyl sulfate, alkyl arylsulfonate, polyethylene glycol alkyl ether, polyoxyethylene alkyl aryl ether), wetting agent (e.g. dodecyl benzenesulfonate, lauryl sulfate), may be incorporated into the preparations. Further, the preparations may include extending agents as conventionally employed and/or other fungicides such as, for example, N-(3,5-dichlorophenyl)-1,2-dimethylcyclopropane-1,2-dicarboximide, S-n-butyl S'-p-tert-butylbenzyl N-3-pyridyldithiocarbonimidate, O,O-dimethyl O-2,6-dichloro-4-methylphenyl phosphorothioate, methyl N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylene-bis(dithiocarbamate), zinc dimethylthiocarbamate, manganese ethylene-bis(dithiocarbamate), bis(-dimethylthiocarbamoyl)disulfide, tetrachloroisophthalonitrile, 8-hydroxyquinoline, dodecylguanidine acetate, 5,6-dihydro-2-methyl-1,4-oxathione-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene and the like; and the benzoxa(thia)zolone derivatives (I) also may be used in admixture with insecticides such as, for example, O,O-dimethyl O-4-nitro-m-tolyl) phosphorothioate, O-p-cyanophenyl O,O-dimethyl phosphorothioate, O-p-cyanophenyl O-ethylphenyl phosphonothioate, O,O-dimethyl S-N-methylcarbamoylmethyl phosphorodithioate, 2-methoxy-4H-1,3,2-benzodioxaphosphorine-2-sulfide, O,O-dimethyl S-1-ethoxycarbonyl-1-phenylmethyl phosphorodithioate, α-cyano-3-phenoxybenzyl 2-(4-chlorophenyl)isovalerate, 3-phenoxybenzyl 2,2-dimethyl-3-(2,2-dichlorovinyl)cyclopropanecarboxylate, 3-phenoxybenzyl chrysanthemate and the like; and, in every case, no controlling effects of individual chemicals are decreased. Accordingly, simultaneous control of two or more injurious fungi and insects is possible. In addition thereto, they may be used in admixture with such agricultural chemicals as nematocides and miticides and with fertilizers.

The foregoing preparations generally contain 0.1 to 95.0% by weight, preferably 0.2 to 90.0% by weight of the active ingredient (including other ingredient mixed). A suitable amount of the preparations applied is generally 10 g. to 1000 g./10 are, and the concentration of the preparations applied is preferably within the range of 0.001 to 0.1% by weight. Since, however, the amount and concentration depend upon the preparation forms, application times, application methods, application sites, diseases and crops, they may be properly increased or decreased irrespective of the aforesaid ranges.

Practical embodiments of the fungicidal composition according to the present invention are illustratively shown in the following examples, wherein parts and % are by weight.

PREPARATION EXAMPLE 1 DUST

2 Parts of the compound (8) and 98 parts of clay were thoroughly pulverized and mixed together to obtain a dust containing 2% of the active ingredient. In application, the dust was dusted as such.

PREPARATION EXAMPLE 2 DUST

3 Parts of the compound (4) and 97 parts of talc were thoroughly pulverized and mixed together to obtain a dust containing 3% of the active ingredient. In application, the dust was dusted as such.

PREPARATION EXAMPLE 3 WETTABLE POWDER

50 Parts of the compound (1), 2.5 parts of a wetting agent of the dodecylbenzenesulfonate, 2.5 parts of a dispersing agent of the sodium lignosulfonate and 45 parts of diatomaceous earth were thoroughly pulverized and mixed together to obtain a wettable powder containing 50% of the active ingredient. In application, the wettable powder was diluted with water, and the resulting solution was sprayed.

PREPARATION EXAMPLE 4 EMULSIFIABLE CONCENTRATE

10 Parts of the compound (2), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

PREPARATION EXAMPLE 5 GRANULE

5 Parts of the compound (10), 93.5 parts of clay and 1.5 parts of a binder of the polyvinyl alcohol type were thoroughly pulverized and mixed together, kneaded with water and then granulated and dried to obtain a granule containing 5% of the active ingredient. In application, the granule was applied as it is or may be mixed with soil.

PREPARATION EXAMPLE 6 FLOATING TYPE GRANULE

10 Parts of the compound (2) is sprayed on 85 parts of pumice having an adjusted particle size of 16 to 32 mesh to allow the compound to soak into the pumice. Thereafter, 5 parts of liquid paraffin is further aprayed thereon to obtain a floating type granule containing 10% of active ingredient. In application, the granule was applied as it is.

PREPARATION EXAMPLE 7 COATING TYPE GRANULE

10 Parts of the compound (5) is sprayed on 77 parts of silica sand having an adjusted particle size of 16 to 32 mesh, and then 3 parts of a 10% aqueous polyvinyl alcohol solution is further sprayed thereon. The mixture is blended with 10 parts of white carbon to obtain a coating type granule containing 10% of active ingredient. In application, the granule was applied as it is.

PREPARATION EXAMPLE 8 GRANULE

10 Parts of the compound (5), 30 parts of bentonite, 1 part of calcium lignosulfonate, 0.1 part of sodium laurylsulfate and 58.9 parts of clay are mixed. The mixture is kneaded with the addition of water, granulated through a screen of 7 mm. in mesh size and dried. Thus, a granule containing 10% of active ingredient is obtained. In application, the granule may be applied as it is or in the form of aqueous dilute solution.

PREPARATION EXAMPLE 9 WATER-SURFACE-SPREADING OIL-BASED LIQUID

1 Part of the compound (2), 10 parts of polyoxypropylene glycol monoether and 89 parts of kerosene are mixed to obtain a water-surface-spreading oil-based liquid was applied as it is.

Some of the test results which support the fungicidal effects of the benzoxa(thia)zole derivatives (I) are shown in the following Test Examples wherein part(s) are by weight. In these Test Examples the compound numbers of the test compounds according to this invention correspond to those shown in Table 1, while the compound numbers of the known test compounds for comparison correspond to those shown in the following Table 2.

TABLE 2

| Compound No. | Chemical structure | Literature or Synthetic method |
|---|---|---|
| i | benzothiazolone, N-H | Pharmazie (1964) 281–283 |
| ii | benzothiazolone, N-CH$_3$ | " |
| iii | benzothiazolone, N-C$_2$H$_5$ | " |
| iv | benzothiazolone, N-CH$_2$Cl | " |
| v | benzoxazolone, N-SCCl$_3$ | Japanese Patent Publication No. 11518/1965 |
| vi | 5-CH$_3$-benzoxazolone, N-SCCl$_3$ | Japanese Patent Publication No. 11518/1965 |
| vii | 5,7-Cl$_2$-benzoxazolone, N-SCCl$_3$ | Japanese Patent Publication No. 11518/1965 |
| viii | benzoxazolone, N-H | Yakugaku Zasshi vol. 79, 931–933 |
| ix | benzothiazole-2-thione, N-CH$_3$ | Chem. Abst. 85 122816w |
| x | benzothiazole-2-thione, N-C$_2$H$_5$ | Chem. Abst. 83 P50807c |
| xi | benzoxazole-2-thione, N-CH$_3$ | Chem. Abst. 83 146678n |
| xii | 7-CH$_3$-benzoxazole-2-thione, N-H | This compound is obtainable by the process of the present invention. |
| xiii | benzoxazole-2-thione, N-C$_2$H$_5$ | Chem. Abst. 83 P9577q |
| xiv | 7-Cl-benzoxazole-2-thione, N-H | This compound is obtainable by the process of the present invention. |
| xv | 7-CH$_3$-benzothiazole-2-thione, N-H | This compound is obtainable by the process as described in Bull. Soc. Chim. Fr. 1973 3044–3051. |
| xvi | 7-Cl-benzothiazole-2-thione, N-H | This compound is obtainable by the process as described in Bull. Soc. Chim. Fr. 1973 3044–3051. |

TEST EXAMPLE 1 RICE BLAST CONTROLLING EFFECT—FOLIAR APPLICATION (PREVENTIVE EFFECT)

To rice plants (Kinki No. 33, 4–5 leaves stage) cultivated in pots of 9 cm. in diameter, test compounds in the form of emulsifiable concentrates prepared according to the method described in Preparation example 4 were diluted with water and spray-applied by means of spray gun in an amount of 15 ml/pot. After one day from said spraying, a spore suspension of *Pyricularia oryzae* was spray-inoculated onto the plants and the inoculated pots were placed in a constant temperature room maintained at 24°–26° C. and a humidity of more than 90%. After 4 days standing, disease severity was determined by the percentage of infected leaf area and examined the control effect. The results are shown in the following Table 3. Disease control was calculated by using the following equation.

$$\text{Disease severity} = \frac{\Sigma(\text{infection index} \times \text{number of leaves})}{8 \times \text{total number of leaves observed}} \times 100$$

| infection index | % of leaf area infected |
|---|---|
| 0 | 0% (none) |
| 1 | les than 10% |
| 2 | 10% to less than 25% |
| 4 | 25% to less than 55% |
| 8 | 55% to 100% |

$$\text{Disease control (\%)} = \left(1 - \frac{\text{disease severity in treated plot}}{\text{disease severity in untreated plot}}\right) \times 100$$

TABLE 3

| Test compound | Concentration of active ingredient (ppm) | Disease control (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| i | 500 | 0 |
| ii | 500 | 5 |
| iii | 500 | 5 |
| iv | 500 | 0 |
| v | 500 | 10 |
| vi | 500 | 10 |
| vii | 500 | 5 |
| viii | 500 | 0 |
| ix | 500 | 0 |
| x | 500 | 0 |
| xi | 500 | 0 |
| xii | 500 | 0 |
| xiii | 500 | 0 |
| xiv | 500 | 0 |
| xv | 500 | 3 |
| xvi | 500 | 0 |
| commercial fungicide* | 500 | 90 |
| untreated | — | 0 |

*O,O—diisopropyl S—benzyl phosphorothiolate (48% emulsifiable concentrate)

TEST EXAMPLE 2 RICE BLAST CONTROLLING EFFECT—FOLIAR APPLICATION (RESIDUAL EFFECT)

To rice plants (Kinki No. 33, 4–5 leaves stage) cultivated in pots of 9 cm. in diameter, test compounds in the form of emulsifiable concentrates prepared according to the method described in Preparation example 4 were diluted with water and applied by means of spray gun in an amount of 15 ml. per pot. After 4 days from said spraying, a spore suspension of *Pyricularia oryzae* was spray-inoculated onto the plants and the inoculated pots were placed in a constant temperature room maintained at 24°–26° C. and a humidity of more than 90%. After 4 days standing, disease severity was determined by the percentage of infected leaf area and examined control effects of the tested compounds. The results are shown in the following Table 4. The calculation of disease severity and of control % were carried out as in Test Example 1.

TABLE 4

| Test compound | Concentration of active ingredient (ppm) | Disease control (%) |
|---|---|---|
| 1 | 500 | 100 |
| 2 | 500 | 100 |
| 3 | 500 | 95 |
| 4 | 500 | 100 |
| 5 | 500 | 100 |
| 6 | 500 | 90 |
| 7 | 500 | 100 |
| 8 | 500 | 100 |
| 9 | 500 | 95 |
| 10 | 500 | 100 |
| 11 | 500 | 100 |
| 12 | 500 | 95 |
| 13 | 500 | 100 |
| 14 | 500 | 100 |
| 15 | 500 | 100 |
| 16 | 500 | 100 |
| i | 500 | 0 |
| ii | 500 | 0 |
| iii | 500 | 0 |
| iv | 500 | 0 |
| v | 500 | 0 |
| vi | 500 | 0 |
| vii | 500 | 0 |
| viii | 500 | 0 |
| ix | 500 | 0 |
| x | 500 | 0 |
| xi | 500 | 0 |
| xii | 500 | 0 |
| xiii | 500 | 0 |
| xiv | 500 | 0 |
| xv | 500 | 0 |
| xvi | 500 | 0 |
| commercial fungicide* | 500 | 50 |
| untreated | — | 0 |

*O—ethyl S,S—diphenyl dithiophosphate (30% emulsifiable concentrate)

TEST EXAMPLE 3 RICE BLAST CONTROLLING EFFECT—SUBMERGED APPLICATION

To rice plants (Kinki No. 33, 5–6 leaves stage) cultivated under flooded conditions in Wagner pots (1/5000 are), test compounds in the form of granules prepared according to the method described in Preparation example 5 were submerged-applied. The test granules were scattered uniformly on the surface of water in an amount equivalent to 500 g. of active ingredient per 10 ares, and the pots were maintained at a depth of 4–5 cm. for defined period of time before inoculation with test microorganisms, in a green house. After 4 days and 30 days from said application, a spore suspension of *Pyricularia oryzae* was spray-inoculated onto the plants and the inoculated pots were placed in a constant temperature room maintained at 24°–26° C. and a humidity of more than 90%. After 4 days standing, disease severity was examined by observing the percentage of infected leaf area and determined the control effects as in Test Example 1. The results are shown in the following Table 5.

TABLE 5

| Test compound | Disease control (%) | |
| --- | --- | --- |
| | Treated at 4 days before inoculation | Treated at 30 days before inoculation |
| 1 | 100 | 100 |
| 2 | 100 | 100 |
| 3 | 100 | 90 |
| 7 | 100 | 100 |
| 8 | 100 | 100 |
| 9 | 100 | 90 |
| 10 | 100 | 100 |
| 11 | 100 | 100 |
| 12 | 100 | 95 |
| 13 | 100 | 100 |
| 14 | 100 | 100 |
| 15 | 100 | 95 |
| 16 | 100 | 95 |
| i | 0 | 0 |
| ii | 0 | 0 |
| iii | 0 | 0 |
| iv | 0 | 0 |
| v | 0 | 0 |
| vi | 0 | 0 |
| vii | 0 | 0 |
| viii | 0 | 0 |
| xi | 0 | 0 |
| xii | 0 | 0 |
| xiii | 0 | 0 |
| xiv | 0 | 0 |
| commercial fungicide* | 90 | 45 |
| untreated | 0 | 0 |

*O,O—diisopropyl S—benzyl phosphorothiolate (17% granule)

TEST EXAMPLE 4 RICE BLAST CONTROLLING EFFECT—SOIL APPLICATION TEST

To rice plants (Kinki No. 33, 5-6 leaves stage) cultivated in Wagner pots (1/5000 are), test compounds in the form of emulsifiable concentrates prepared according to the method described in Preparation example 4 were applied to soil. Each emulsifiable concentrate was diluted with water and applied on the surface of soil in an amount equivalent to 500 g. active ingredient per 10 ares. After 4 days and 30 days, a spore suspension of Pyricularia oryzae was spray-inoculated onto the plant and the inoculated pots were placed in a constant temperature room maintained at 24°-26° C. and a humidity of more than 90%. After 4 days standing, disease severity and control effect were determined as in Test Example 1. The results are shown in the following Table 6.

TABLE 6

| Test compound | Disease control (%) | |
| --- | --- | --- |
| | Treated at 4 days before inoculation | Treated at 30 days before inoculation |
| 1 | 100 | 100 |
| 2 | 100 | 100 |
| 3 | 100 | 95 |
| 7 | 100 | 100 |
| 8 | 100 | 100 |
| 9 | 100 | 95 |
| 10 | 100 | 100 |
| 11 | 100 | 100 |
| 12 | 100 | 97 |
| 13 | 100 | 100 |
| 14 | 100 | 100 |
| 15 | 100 | 90 |
| 16 | 100 | 90 |
| i | 0 | 0 |
| ii | 0 | 0 |
| iii | 0 | 0 |

TABLE 6-continued

| Test compound | Disease control (%) | |
| --- | --- | --- |
| | Treated at 4 days before inoculation | Treated at 30 days before inoculation |
| iv | 0 | 0 |
| v | 0 | 0 |
| vi | 0 | 0 |
| vii | 0 | 0 |
| viii | 0 | 0 |
| xi | 0 | 0 |
| xii | 0 | 0 |
| xiii | 0 | 0 |
| xiv | 0 | 0 |
| commercial fungicide* | 95 | 40 |
| untreated | 0 | 0 |

*O,O—diisopropyl S—benzyl phosphorothiolate (48% emulsifiable concentrate)

TEST EXAMPLE 5 RICE BLAST CONTROLLING EFFECT—TRANSPLANT FLAT APPLICATION TEST

To rice plant (Kinki No. 33, 2-2.5 leaves stage) cultivated in a 30×60×3 cm. transplant flat, test compounds in the form of granules prepared according to the method described in Preparation example 5 were applied to soil. The test granules were scattered uniformly over the soil surface in an amount equivalent to 20 g. of active ingredient per transplant flat. After 24 hours, treated plants were removed from the flats by cutting 1 cm² blocks of soil and hand transplanting roots plus soil into flooded conditions in Wagner pots (1/5000 are). The pots were maintained at a depth of 4-5 cm. for defined period of time before inoculation with test microorganisms, in a green house. After 60 days from said medication, a spore suspension of Pyricularia oryzae was spray-inoculated onto the plants and the inoculated pots were placed in a constant temperature room maintained at 24°-26° C. and a humidity of more than 90%. After 4 days standing, disease severity was examined by observing the percentage of infected leaf area and determined and control effects as in Test Example 1. The results are shown in the following Table 7.

TABLE 7

| Test compound | Disease control (%) |
| --- | --- |
| 1 | 100 |
| 2 | 100 |
| 3 | 85 |
| 7 | 100 |
| 8 | 100 |
| 9 | 90 |
| 10 | 100 |
| 11 | 100 |
| 12 | 95 |
| 13 | 100 |
| 14 | 100 |
| 15 | 100 |
| 16 | 100 |
| commercial fungicide* | 55 |
| untreated | 0 |

*O,O—diisopropyl S—benzyl phosphorothiolate (17% granule)

TEST EXAMPLE 6 HELMINTHOSPORIUM LEAF SPOT CONTROLLING EFFECT—FOLIAR APPLICATION TEST (PREVENTIVE EFFECT)

To rice plants (Kinki No. 33, 4-5 leaves stage) cultivated in pots (9 cm. in diameter, 4 plants per pot), test compounds in the form of emulsifiable concentrate prepared according to the method described in Preparation example 4 were diluted with water and applied by means of spray gun in an amount of 15 ml. per pot. After one day from said spraying, mycerial disk (5 mm. in diameter) of *Helminthosporium sigmoideum* cultured in PSA medium was attached to the sheath portion of each stem, and the inoculated pots were placed in a constant temperature room maintained at 28° C. After 4 days standing, disease severity was determined by measuring the infected sheath length and using the following equation.

$$\text{Disease severity} = \frac{\Sigma(\text{infection index} \times \text{number of stem})}{3 \times \text{total number of stems observed}} \times 100$$

| Infection index | Infected sheath length |
|---|---|
| 0 | 0 (none) |
| 1 | slightly observed, but negligible |
| 2 | less than 1 cm. |
| 3 | more than 1 cm. |

The control effect was determined as in Test Example 1 and the results are shown in the following Table 8.

TABLE 8

| Test compound | Concentration of active ingredient (ppm) | Disease control (%) |
|---|---|---|
| 1 | 500 | 100 |
| 2 | 500 | 100 |
| 3 | 500 | 95 |
| 7 | 500 | 100 |
| 8 | 500 | 100 |
| 9 | 500 | 90 |
| 10 | 500 | 100 |
| 11 | 500 | 100 |
| 12 | 500 | 95 |

TABLE 8-continued

| Test compound | Concentration of active ingredient (ppm) | Disease control (%) |
|---|---|---|
| commercial fungicide* | 500 | 88 |
| untreated | — | 0 |

*O—ethyl S,S—diphenyl dithiophosphate (30% emulsifiable concentrate)

What is claimed is:

1. A compound of the formula:

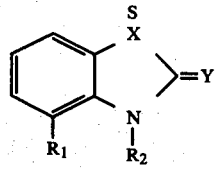

wherein $R_1$ is a halogen atom or methyl group, $R_2$ is a methyl or ethyl group and X is a sulfur atom and Y is an oxygen atom.

2. The compound according to claim 1, wherein $R_1$ and $R_2$ are each a methyl group.

3. The compound according to claim 1, wherein $R_1$ is a chlorine atom, $R_2$ is a methyl group.

4. An agricultural fungicidal composition which comprises as an active ingredient an agricultural fungicidally effective amount of the compound according to claim 1 and an inert carrier or diluent.

5. A method for controlling *phytopathogenic fungi* which comprises applying an effective amount *against phytopathogenic fungi* of the compound according to claim 1 to the fungi.

6. The method according to claim 5, wherein fungus is *Pyricularia oryzae*.

7. The method according to claim 5, wherein fungus is *Helminthosporium sigmoideum*.